United States Patent
Ritland

(10) Patent No.: US 7,214,186 B2
(45) Date of Patent: *May 8, 2007

(54) METHOD AND DEVICE FOR RETRACTOR FOR MICROSURGICAL INTERMUSCULAR LUMBAR ARTHRODESIS

(76) Inventor: Stephen Ritland, 1150 N. San Francisco St., Flagstaff, AZ (US) 86001

(*) Notice: Subject to any disclaimer, the term of this patent is extended or adjusted under 35 U.S.C. 154(b) by 364 days.

This patent is subject to a terminal disclaimer.

(21) Appl. No.: 10/745,068

(22) Filed: Dec. 22, 2003

(65) Prior Publication Data

US 2004/0138534 A1   Jul. 15, 2004

Related U.S. Application Data

(63) Continuation of application No. 09/969,138, filed on Oct. 1, 2001, now Pat. No. 6,692,434.

(60) Provisional application No. 60/236,584, filed on Sep. 29, 2000.

(51) Int. Cl.
*A61B 17/02* (2006.01)
(52) U.S. Cl. .................... 600/217; 600/210
(58) Field of Classification Search ........ 600/201, 600/210, 213, 214, 217, 219, 235
See application file for complete search history.

(56) References Cited

U.S. PATENT DOCUMENTS

| | | |
|---|---|---|
| 569,839 A | 10/1896 | Roeloffs |
| 3,467,079 A * | 9/1969 | James .................. 600/210 |
| 3,470,872 A | 10/1969 | Grieshaber |
| 3,875,595 A | 4/1975 | Froning |
| 4,041,939 A | 8/1977 | Hall |
| 4,232,660 A | 11/1980 | Coles .................. 600/210 |
| 4,440,168 A | 4/1984 | Warren |
| 4,481,947 A | 11/1984 | Chester .................. 128/303 R |
| 4,545,374 A | 10/1985 | Jacobson |
| 4,573,448 A | 3/1986 | Kambin |
| 4,617,922 A | 10/1986 | Griggs .................. 128/92 YS |
| 4,620,460 A | 11/1986 | Gonzales, Jr. |
| 4,686,972 A | 8/1987 | Kurland .................. 606/96 |
| 4,736,738 A | 4/1988 | Lipovsek |
| 4,743,260 A | 5/1988 | Burton |

(Continued)

FOREIGN PATENT DOCUMENTS

EP   0820731   5/2003

(Continued)

OTHER PUBLICATIONS

Web pages, http://www.brainlab.com, Apr. 2, 2002; 5 pp.

(Continued)

*Primary Examiner*—Cary E. O'Connor
(74) *Attorney, Agent, or Firm*—Sheridan Ross P.C.

(57) ABSTRACT

An instrument useful in performing lumbar arthrodesis with a minimal approach which spares the lumbar muscles from surgical disruption and includes one of two retractor designs having blades angled approximately 90° with respect to each respective retractor handle. One blade is bent at an end portion thereof in a direction away from the handle portion. The other blade has first and second blade faces, with the second face having at least two toothed structures located thereon.

9 Claims, 3 Drawing Sheets

U.S. PATENT DOCUMENTS

| | | | | |
|---|---|---|---|---|
| 4,747,394 | A | 5/1988 | Watanabe | 128/20 |
| 4,798,111 | A | 1/1989 | Cheeseman | |
| 4,803,976 | A | 2/1989 | Frigg | |
| 4,817,587 | A | 4/1989 | Janese | 128/20 |
| 4,862,891 | A | 9/1989 | Smith | |
| 4,863,423 | A | 9/1989 | Wallace | |
| 4,882,958 | A | 11/1989 | McNeeley | |
| 4,995,875 | A * | 2/1991 | Coes | 606/90 |
| 5,002,542 | A | 3/1991 | Frigg | |
| 5,002,576 | A | 3/1991 | Fuhrmann et al. | |
| 5,026,373 | A | 6/1991 | Ray et al. | |
| 5,030,220 | A | 7/1991 | Howland | |
| 5,035,232 | A | 7/1991 | Lutze et al. | 128/20 |
| 5,048,379 | A | 9/1991 | Gramera | |
| 5,052,373 | A | 10/1991 | Michelson | 128/20 |
| 5,055,104 | A | 10/1991 | Ray | |
| 5,084,043 | A | 1/1992 | Hertzmann | |
| 5,098,435 | A | 3/1992 | Stednitz | |
| 5,106,376 | A | 4/1992 | Mononen | |
| 5,129,900 | A | 7/1992 | Asher et al. | |
| 5,133,720 | A | 7/1992 | Greenberg | 606/96 |
| 5,135,525 | A | 8/1992 | Biscoping | |
| 5,148,724 | A | 9/1992 | Rexford | |
| 5,158,543 | A | 10/1992 | Lazarus | |
| 5,195,541 | A | 3/1993 | Obenchain | |
| 5,275,600 | A | 1/1994 | Allard et al. | |
| 5,275,611 | A | 1/1994 | Behl | |
| 5,279,567 | A | 1/1994 | Ciaglia | |
| 5,292,309 | A | 3/1994 | Van Tassel | |
| 5,303,694 | A | 4/1994 | Mikhail | 128/20 |
| 5,306,309 | A | 4/1994 | Wagner et al. | |
| 5,312,360 | A | 5/1994 | Behl | |
| 5,312,405 | A | 5/1994 | Korotko et al. | |
| 5,356,413 | A | 10/1994 | Martins et al. | |
| 5,363,841 | A | 11/1994 | Coker | 128/20 |
| 5,415,661 | A | 5/1995 | Holmes | |
| 5,431,639 | A | 7/1995 | Shaw | |
| 5,431,651 | A | 7/1995 | Goble | |
| D361,381 | S | 8/1995 | Koros et al. | D24/135 |
| 5,439,464 | A | 8/1995 | Shapiro | |
| 5,466,238 | A | 11/1995 | Lin | |
| 5,472,426 | A | 12/1995 | Bonati | |
| 5,474,555 | A | 12/1995 | Puno et al. | |
| 5,484,440 | A | 1/1996 | Allard | |
| 5,489,274 | A | 2/1996 | Chu | |
| 5,489,308 | A | 2/1996 | Kuslich et al. | |
| 5,512,038 | A | 4/1996 | O'Neal et al. | 600/210 |
| 5,558,622 | A * | 9/1996 | Greenberg | 600/237 |
| 5,565,502 | A | 10/1996 | Glimcher et al. | |
| 5,591,166 | A | 1/1997 | Bernhardt et al. | |
| 5,591,235 | A | 1/1997 | Kuslich | |
| 5,593,409 | A | 1/1997 | Michelson | |
| 5,601,550 | A | 2/1997 | Esser | 606/54 |
| 5,611,778 | A | 3/1997 | Brinon | |
| 5,628,740 | A | 5/1997 | Mullane | |
| 5,643,263 | A | 7/1997 | Simonson | |
| 5,643,264 | A | 7/1997 | Sherman et al. | |
| 5,645,599 | A | 7/1997 | Samani | |
| 5,683,463 | A | 11/1997 | Godefroy et al. | |
| 5,687,739 | A | 11/1997 | McPherson | |
| 5,690,632 | A | 11/1997 | Schwartz et al. | |
| 5,691,397 | A | 11/1997 | Glimcher et al. | |
| 5,702,455 | A | 12/1997 | Saggar | |
| 5,716,415 | A | 2/1998 | Steffee | 623/17 |
| 5,725,528 | A | 3/1998 | Errico et al. | |
| 5,735,899 | A | 4/1998 | Schwartz et al. | |
| 5,743,853 | A | 4/1998 | Lauderdale | 600/210 |
| 5,746,720 | A | 5/1998 | Stouder, Jr. | |
| 5,746,741 | A | 5/1998 | Kraus et al. | |
| 5,752,957 | A | 5/1998 | Ralph et al. | |
| 5,766,221 | A | 6/1998 | Benderev et al. | 606/232 |
| 5,766,253 | A | 6/1998 | Brosnahan, III | |
| 5,782,832 | A | 7/1998 | Larsen et al. | |
| 5,785,710 | A | 7/1998 | Michelson | |
| 5,792,044 | A | 8/1998 | Foley | |
| 5,800,435 | A | 9/1998 | Errico et al. | |
| D399,955 | S | 10/1998 | Koros et al. | D24/135 |
| 5,816,257 | A | 10/1998 | Chin | |
| 5,827,328 | A | 10/1998 | Buttermann | |
| 5,836,948 | A | 11/1998 | Zucherman et al. | |
| RE36,020 | E | 12/1998 | Moore et al. | |
| 5,851,207 | A | 12/1998 | Cesarone | |
| 5,860,977 | A | 1/1999 | Zucherman et al. | |
| 5,865,847 | A | 2/1999 | Kohrs et al. | |
| 5,865,848 | A | 2/1999 | Baker | |
| 5,876,404 | A | 3/1999 | Zucherman et al. | |
| 5,882,344 | A | 3/1999 | Stouder, Jr. | |
| 5,885,285 | A | 3/1999 | Simonson | |
| 5,885,299 | A | 3/1999 | Winslow et al. | |
| 5,885,300 | A | 3/1999 | Tokuhashi et al. | 606/99 |
| 5,891,147 | A | 4/1999 | Moskovitz et al. | 606/79 |
| 5,895,352 | A | 4/1999 | Kleiner | 600/206 |
| 5,895,390 | A | 4/1999 | Moran et al. | 606/96 |
| 5,897,593 | A | 4/1999 | Kohrs et al. | 623/17 |
| 5,899,901 | A | 5/1999 | Middleton | |
| 5,902,231 | A | 5/1999 | Foley | |
| 5,906,616 | A | 5/1999 | Pavlov et al. | |
| 5,913,818 | A | 6/1999 | Co et al. | 600/204 |
| 5,928,139 | A | 7/1999 | Koros | |
| 5,928,233 | A | 7/1999 | Apfelbaum et al. | |
| 5,944,658 | A | 8/1999 | Koros et al. | 600/232 |
| 5,954,635 | A | 9/1999 | Foley | |
| 5,954,671 | A | 9/1999 | O'Neil | |
| 5,967,970 | A | 10/1999 | Cowan | |
| 5,968,098 | A | 10/1999 | Winslow | |
| 5,971,920 | A | 10/1999 | Nagel | |
| 5,976,146 | A | 11/1999 | Ogawa | |
| 5,984,924 | A | 11/1999 | Asher et al. | |
| 5,996,447 | A | 12/1999 | Bayouth | |
| 5,997,539 | A | 12/1999 | Errico et al. | |
| 6,007,487 | A | 12/1999 | Foley et al. | 600/235 |
| 6,010,520 | A | 1/2000 | Pattison | |
| 6,045,579 | A | 4/2000 | Hochshuler et al. | |
| 6,048,342 | A | 4/2000 | Zucherman et al. | |
| 6,050,997 | A | 4/2000 | Mullane | |
| 6,063,088 | A | 5/2000 | Winslow | 606/61 |
| 6,068,630 | A | 5/2000 | Zucherman et al. | |
| 6,074,390 | A | 6/2000 | Zucherman et al. | |
| 6,074,393 | A | 6/2000 | Sitoto | |
| 6,080,155 | A | 6/2000 | Michelson | 606/61 |
| 6,080,193 | A | 6/2000 | Hochshuler et al. | |
| 6,081,741 | A | 6/2000 | Hollis | |
| 6,083,225 | A | 7/2000 | Winslow et al. | 606/61 |
| 6,090,112 | A | 7/2000 | Zucherman et al. | |
| 6,102,948 | A | 8/2000 | Brosnahan, III | |
| 6,113,602 | A | 9/2000 | Sand | 606/61 |
| 6,117,137 | A | 9/2000 | Halm et al. | |
| 6,117,174 | A | 9/2000 | Nolan | |
| 6,120,434 | A | 9/2000 | Kimura | |
| 6,120,506 | A | 9/2000 | Kohrs et al. | 606/80 |
| 6,123,705 | A | 9/2000 | Michelson | |
| 6,123,706 | A | 9/2000 | Lange | |
| 6,132,430 | A | 10/2000 | Wagner | |
| D433,296 | S | 11/2000 | Yamakawa | |
| 6,149,652 | A | 11/2000 | Zucherman et al. | |
| 6,149,686 | A | 11/2000 | Kuslich et al. | |
| 6,152,871 | A | 11/2000 | Foley | |
| 6,152,926 | A | 11/2000 | Zucherman et al. | |
| 6,156,006 | A | 12/2000 | Brosens | |
| 6,156,038 | A | 12/2000 | Zucherman et al. | |
| 6,159,179 | A | 12/2000 | Simonson | |
| 6,162,170 | A | 12/2000 | Foley | |
| 6,162,236 | A | 12/2000 | Osada | |
| D436,513 | S | 1/2001 | Yamakawa | |

| | | |
|---|---|---|
| 6,176,823 B1 | 1/2001 | Foley |
| 6,179,838 B1 | 1/2001 | Fiz |
| D438,074 S | 2/2001 | Marr |
| 6,183,471 B1 | 2/2001 | Zucherman et al. |
| 6,190,387 B1 | 2/2001 | Zucherman et al. |
| 6,190,414 B1 | 2/2001 | Young et al. |
| 6,197,002 B1 | 3/2001 | Peterson |
| 6,206,822 B1 | 3/2001 | Foley |
| 6,206,826 B1 | 3/2001 | Mathews et al. ......... 600/210 |
| 6,206,885 B1 | 3/2001 | Ghahremani et al. ....... 606/96 |
| 6,206,922 B1 | 3/2001 | Zdeblick et al. |
| 6,206,923 B1 | 3/2001 | Boyd et al. |
| 6,210,413 B1 | 4/2001 | Justis et al. |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,235,030 B1 | 5/2001 | Zucherman et al. |
| 6,238,397 B1 | 5/2001 | Zucherman et al. |
| 6,245,072 B1 | 6/2001 | Zdeblick et al. ............. 606/61 |
| 6,248,106 B1 | 6/2001 | Ferree |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro ......................... 606/61 |
| 6,267,764 B1 | 7/2001 | Elberg |
| 6,267,765 B1 | 7/2001 | Taylor et al. |
| 6,270,498 B1 | 8/2001 | Michelson .................. 606/61 |
| 6,283,966 B1 | 9/2001 | Houfburg |
| 6,287,313 B1 | 9/2001 | Sasso |
| 6,290,700 B1 | 9/2001 | Schmotzer |
| 6,293,949 B1 | 9/2001 | Justis et al. |
| 6,296,609 B1 * | 10/2001 | Brau ........................... 600/210 |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. ............ 606/130 |
| 6,354,176 B1 | 3/2002 | Nordlin |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka |
| 6,391,058 B1 | 5/2002 | Kuslich et al. |
| 6,395,033 B1 | 5/2002 | Pepper |
| 6,418,821 B1 | 7/2002 | Yamakawa |
| 6,428,472 B1 | 8/2002 | Haas .......................... 600/206 |
| 6,440,169 B1 | 8/2002 | Elberg et al. |
| 6,443,989 B1 | 9/2002 | Jackson |
| 6,461,330 B1 | 10/2002 | Miyagi |
| D466,766 S | 12/2002 | Marty |
| 6,520,907 B1 | 2/2003 | Foley |
| 6,524,238 B2 | 2/2003 | Velikaris et al. |
| 6,530,926 B1 | 3/2003 | Davison |
| 6,540,756 B1 | 4/2003 | Vaughan |
| 6,551,320 B2 | 4/2003 | Lieberman |
| 6,565,569 B1 | 5/2003 | Assaker et al. |
| 6,692,434 B2 | 2/2004 | Ritland |
| 6,736,816 B2 | 5/2004 | Ritland |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0058948 A1 | 5/2002 | Arlettaz |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0083688 A1 | 5/2003 | Simonson |
| 2003/0083689 A1 | 5/2003 | Simonson |
| 2003/0093078 A1 | 5/2003 | Ritland |
| 2003/0144665 A1 | 7/2003 | Munting |
| 2003/0171749 A1 | 9/2003 | Le Couedic et al. |
| 2003/0171751 A1 | 9/2003 | Ritland |
| 2003/0187431 A1 | 10/2003 | Simonson |
| 2003/0191470 A1 | 10/2003 | Ritland |
| 2003/0220689 A1 | 11/2003 | Ritland |
| 2003/0236447 A1 | 12/2003 | Ritland |
| 2004/0002708 A1 | 1/2004 | Ritland |
| 2004/0106997 A1 | 6/2004 | Lieberson |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |

FOREIGN PATENT DOCUMENTS

| | | |
|---|---|---|
| WO | WO 00/18306 | 4/2000 |
| WO | WO 02/02022 | 1/2002 |
| WO | WO 02/07621 | 1/2002 |
| WO | WO 02/060330 | 8/2002 |
| WO | WO 03/026523 | 4/2003 |
| WO | WO 03/073908 | 9/2003 |
| WO | WO 03/094699 | 11/2003 |
| WO | WO 04/075778 | 9/2004 |
| WO | WO 04/089244 | 10/2004 |

OTHER PUBLICATIONS

Caspar; "Technique of Microsurgery: Microsurgery of the Lumbar Spine: Principles and Techniques in Spine Surgery"; *Aspen Publications*; 1990; 105-122.

Hilton et al.; "Meditronic Sofamor Danek METRX Microdiscectomy Surgical Technique Brochure"; 2000.

Kambin; "Arthroscopic Microdiscectomy: Minimal Intervention in Spinal Surgery"; *National Library of Medicine*; 1991; 67-100.

Kambin; "Percutaneous Posterolateral Discectomy"; *Clinical Orthopaedics and Related Research, Section II*; 145-154119.

Savitz; "Same-Day Microsurgical Arthroscopic Latera-Approach Laser-Assisted (SMALL) Fluoroscopic Discectomy"; *Journal of Neurosurgery*; Jun. 1994; 1039-1045.

Schaffer et al.; "Percutaneous Posterolateral Lumbar Discectomy and Decompression with a 6.9 Millimeter Cannula"; *Journal of Bone and Joint Surgery*; 1991; 822-831.

Sofamor Danek Video Systems Brochure.

Wiltse; "New Uses and Refinements of the Paraspinal Approach to the Lumbar Spine"; *Spine*; 1988; 13(6):696-706.

\* cited by examiner

METHOD AND DEVICE FOR RETRACTOR FOR MICROSURGICAL INTERMUSCULAR LUMBAR ARTHRODESIS

CROSS REFERENCE TO RELATED APPLICATION

This application is a continuation of U.S. patent application Ser. No. 09/969,138 filed on Oct. 1, 2001 and entitled "METHOD AND DEVICE FOR RETRACTOR FOR MICROSURGICAL INTERMUSCULAR LUMBAR ARTHRODESIS", now U.S. Pat. No. 6,692,434, which claimed priority from U.S. Provisional Patent Application No. 60/236,584 filed on Sep. 29, 2000. The entire disclosures of these applications are considered to be part of the disclosure of the present application and are hereby incorporated by reference in their entirety.

FIELD OF THE INVENTION

The present invention is directed to a method and device for microsurgical intermuscular lumbar anthrodesis.

BACKGROUND AND SUMMARY OF THE INVENTION

Results of posterior lumbar fusion have frequently been compromised by residuals from muscular and neurovascular disruption accompanying anthrodesis. An approach along the lateral aspect of the multifidus avoids disruption of the dorsal lumbar musculature and allows for segmental pedicle fixation without disturbing the neurovascular supply to the erector spinae or multifidus. Detachment of the segmental insertion of the multifidus to the mamillary process provides access for a microsurgical transforaminal interbody fusion.

Present techniques of lumbar anthrodesis including instrumentation and interbody fusion provide a reasonable expectation of fusion with surgery, however, outcomes remain limited by pain and adjacent segment failure. To the extent this results from fusion it may be unavoidable. Limitations from denervation, devascularization and disconnection of lumbar musculature and the disruption of musculoskeletal integrity of adjacent segments may be largely avoidable.

There is therefore a long felt, but unsolved need for a method and device in order to perform an instrumented lumbar arthrodesis with a minimal approach which spares the lumbar muscles from surgical disruption.

DETAILED DESCRIPTION OF THE INVENTION

Figure 1:
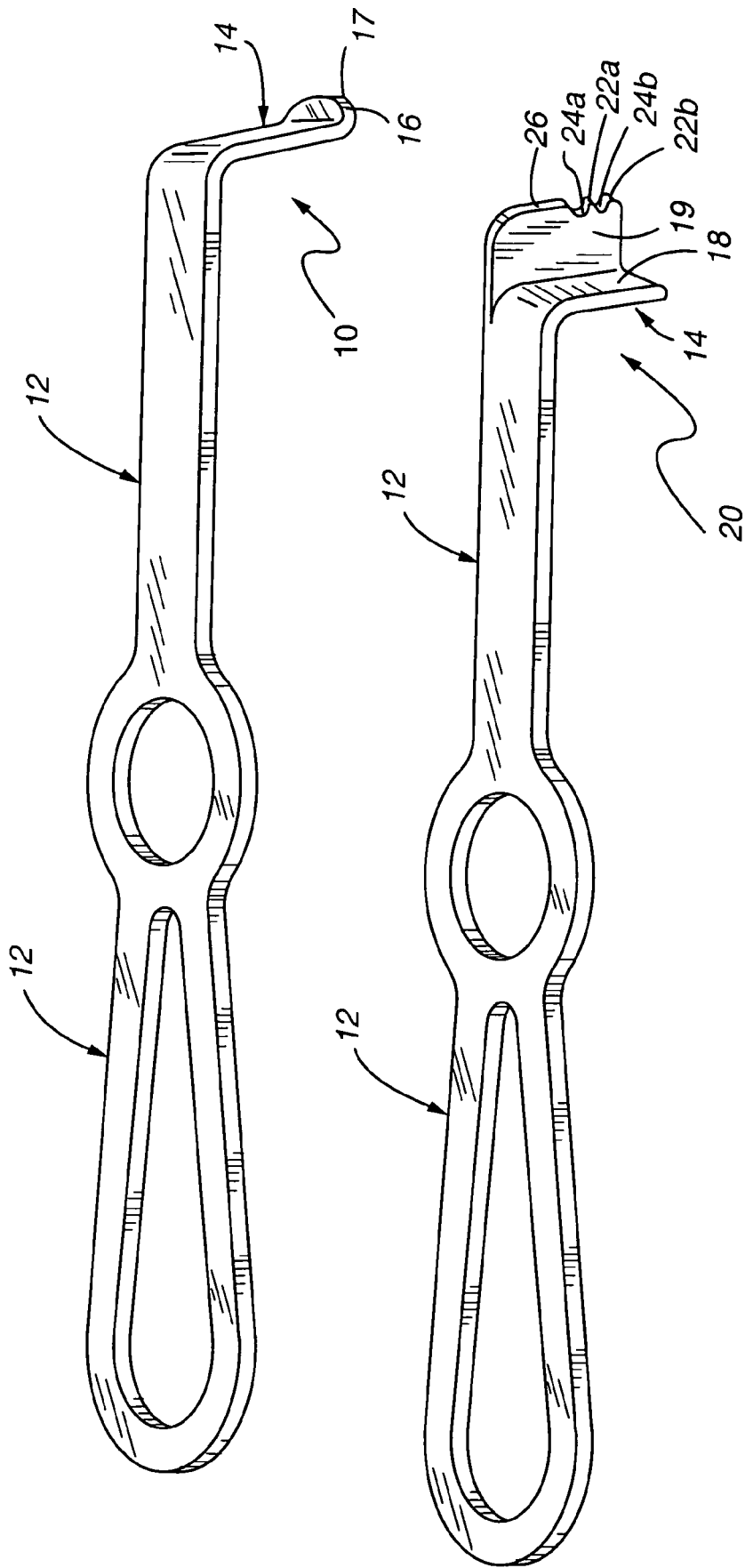
FIG. 1 is a side perspective view of the retractors of the present invention.
Figure 2:
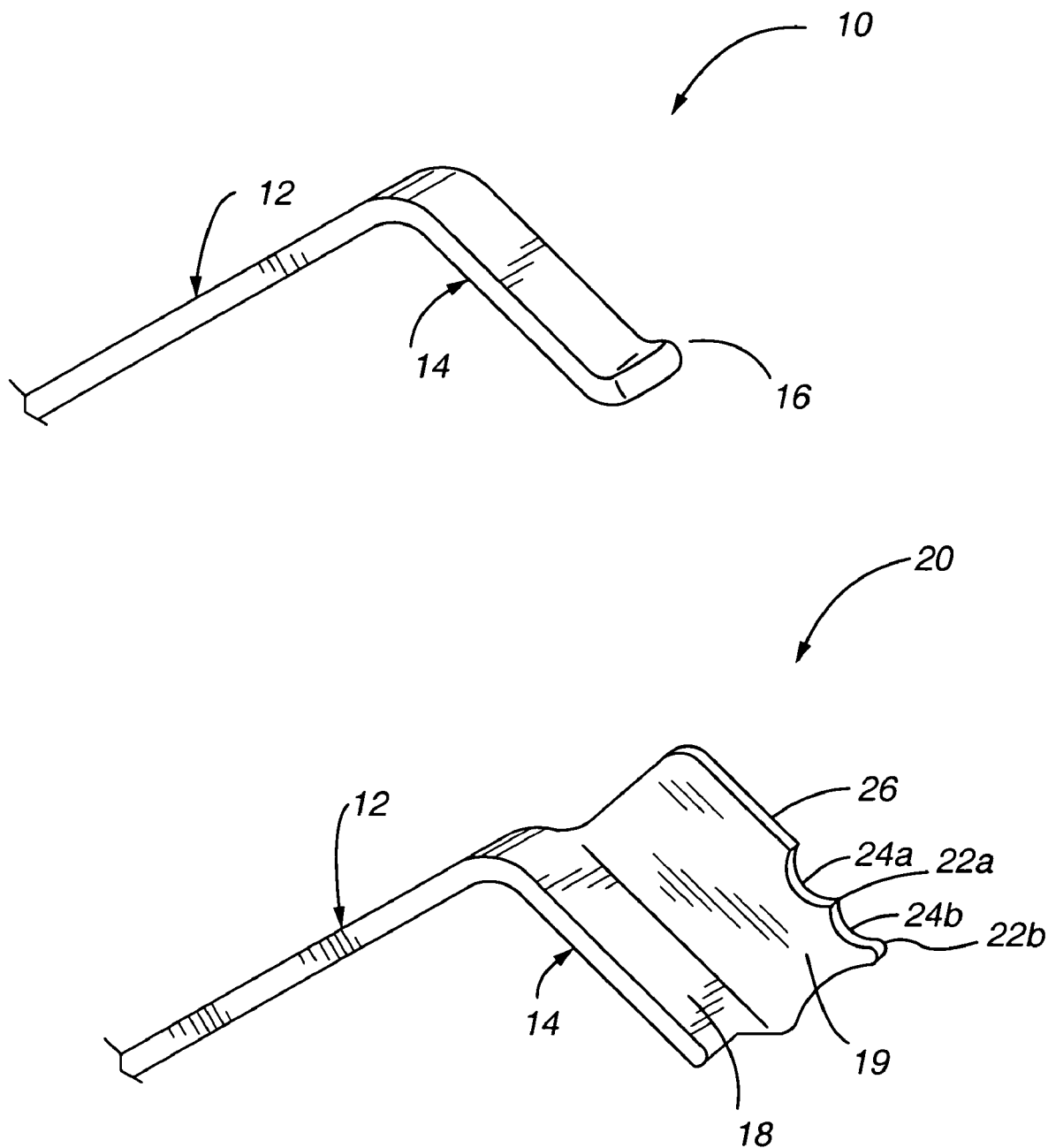
FIG. 2 is a partial perspective view of the retractor blade ends of the retractors of the present invention.
Figure 3:
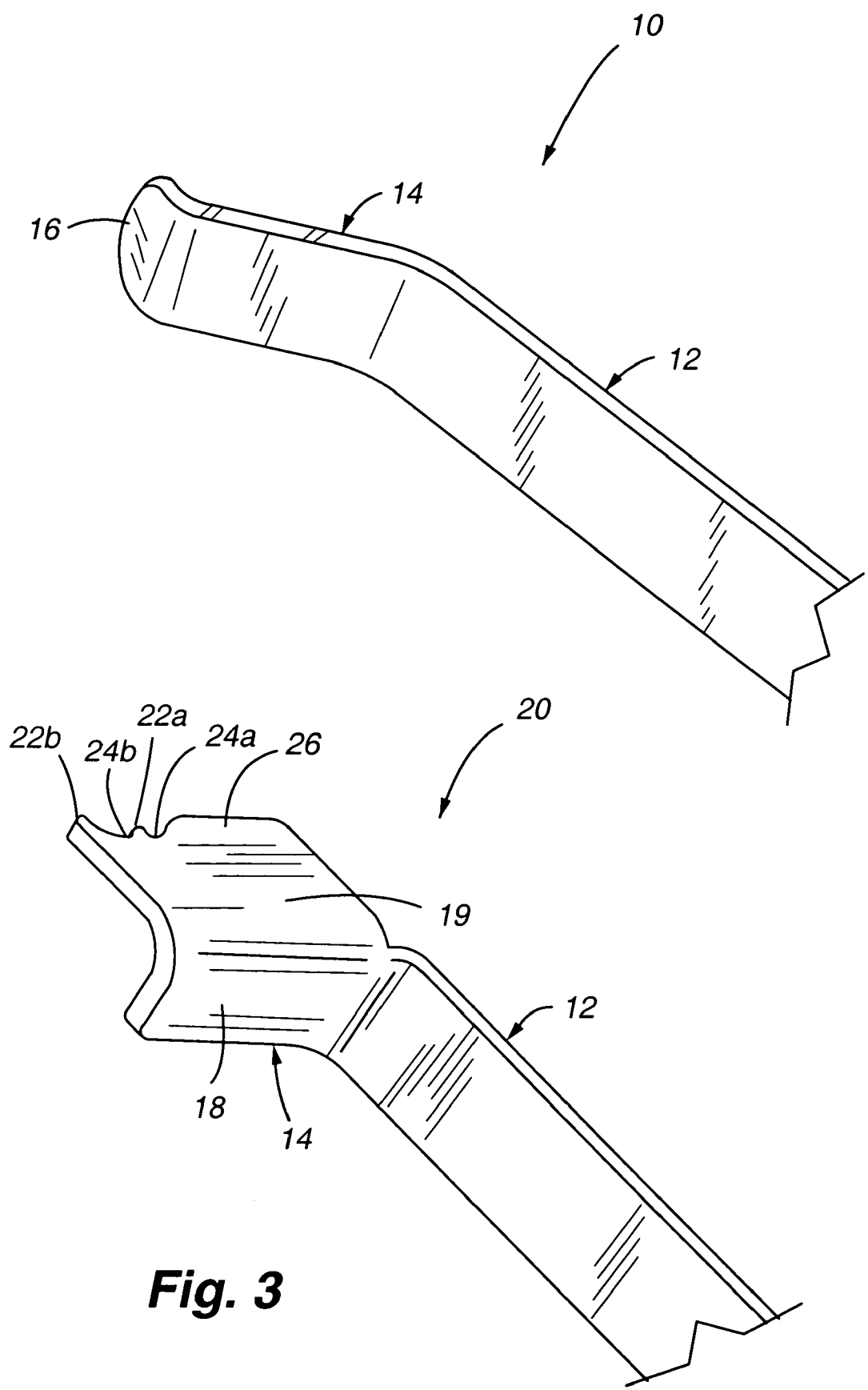
FIG. 3 is a view of the retractor blade ends as depicted in FIG. 2, but viewed from a reverse angle.

The present invention is directed to a method and device for performing an instrumented lumbar interbody fusion utilizing a minimally invasive approach. As set forth herein below and as reflected in the figures, the present invention is generally directed to the use of a tissue retractor 10 for use in lumbar arthrodesis which comprises an elongated retractor 10 having a handle 12 at one end and a retractor blade 14 at a second end, the retractor blade 14 having a hooked forward projecting prominence 16 to engage a lateral facet or muscle, the retractor blade 14 being angled with respect to the handle 12 and having a depth so as to provide adequate retraction when performing a screw placement operation. The forward projecting prominence 16 has a width approximately equal to a width of the retractor blade 14, and has a semi-circular shaped front edge 17. A separate retractor 20 has a similar handle 12 and has a blade 14 angled with respect thereto at approximately a 90° angle. Such retractor blade 14 having first and second faces 18 and 19, respectively, with the first face 18 being substantially perpendicular to the second face 19 and the first face 18 being angled approximately 90° with respect to the handle 12, whereas the second face 19 has at least two co-planar toothed structures 22a and 22b at a position located farthest from the handle end. The toothed structures 22a and 22b are situated adjacent two co-planar indentations 24a and 24b. The toothed structures 22a and 22b, and the indentations 24a and 24b are located along a lower portion of a forward projecting lateral edge 26 of the second face 19. The indentations 24a and 24b are semi-circular in shape. The retractor of the present invention is used in the method as further set forth below.

A surgical approach between the erector spinae and multifidus approaches the lateral facet and superomedial transverse process directly with no muscular detachment and avoids both the medial and lateral branches of the dorsal primary ramus and associated vessels. Orientation is appropriate for direct placement of pedicle fixation with minimal muscular retraction. Mobilization of a 4 to 5 cm midline incision allows direct bilateral exposure. Medial retraction of the multifidus after detaching its tendinous insertion to the mamillary process is simplified by stabilizing the retractor 20 against the rod. Interbody fusion is accomplished via a transforaminal approach. Microsurgical technique allows for coagulation and sharp division of the inferior foraminal vein (or plexus) and retraction of foraminal fat with preservation of undisturbed perineural and epidural tissue planes to minimize potential for fibrosis. Interbody fusion is performed conventionally with bone and or synthetic devices. Use of an intradiscal spreader and securing the opening with the segmental fixation simplifies preparation of the disk space and improves restoration of lordosis with dorsal compression after grafting.

The lumbar musculature posteriorly may be considered as a medial and lateral complex. The bulk of the medial musculature is the multifidus which is supplied by the medial branch of the dorsal primary ramus of the nerve and accompanying vessels as well as the artery related to the pars interarticularis. The bulk of the lateral musculature is the longissimus thoracis and ilocostalis supplied by the intermediate and lateral branches of the dorsal ramus. Approach is the intermuscular plane along the lateral aspect of the multifidus allows direct access to the lateral facet and superomedial transverse process in an area devoid of muscle attachment. While the medial branch traverses the lateral facet to the mamilloaccessory notch and the intermediate and lateral branches penetrate the longissimus and iliocostalis from their ventromedial surface, approach for pedicle screw placement may be consistently accomplished without disturbing nerves or vessels.

After reflection of the thoracolumbar fascia the erector spinae aponeurosis may be divided along the course of its fibers. Some superficial fibers of the multifidus may be seen joining the underside of the ESA. There is a tendency for the longissimus to wrap slightly over the dorsal aspect of the multifidus which may typically be well seen on the preoperative CT or MRI. As one drops down the lateral aspect of the multifidus the tendinous insertion to the mamillary process is typically well seen with a little fat present both in the intermuscular plane and lateral to the facet. Additionally the contrasting course of the longissimus and multifidus is often seen.

In some individuals the bulk of the multifidus in the lower lumbar spine may make for a relatively oblique approach and potentially make it relatively more difficult to approach pathology in the spinal canal. In this situation a muscle splitting approach through the multifidus may still minimize the required exposure.

Once the instrumentation is placed, exposure for the fusion is performed. Dividing the insertion of the multifidus to the mamillary process on the superior articular process of the lower vertebra allows retraction of the multifidus over the facet capsule with no further muscle detachment required. While use of a hand retractor 20 may be adequate to pull the multifidus medial against the spinous process, it is preferable to retract using leverage against the rod or instrumentation. Removal of the inferior articular process and a portion of the superior articular process provides direct access to the foramen. Use of the operating microscope allows for an interbody fusion with exposure and visualization comparable to microdisectomy. Exposure of the superior aspect of the pedicle of the lower level confirms location and allows coagulation and division of the inferior foraminal vein or plexus in a safe location. If the exposure is extended cephalad in this plane, the epidural vessels and fat may be minimally disturbed and retracted preserving the epidural and penineural planes while exposing the disc. There is generally a window 10 to 12 mm in width allowing work in the disc with no retraction of neural elements. Intradiscal fusion may be accomplished conventionally with bone or prosthesis. The use of intradiscal spreaders with temporary fixation from the instrumentation allows for easier work in the disc space and subsequent compression on the graft allows restoration of lordosis. With care it is possible to bridge the foraminal space with graft for posterior facet fusion.

In most cases canal pathology may be adequately treated. One can, however, go to the midline to be sure of adequate decompression. Once the inferior articular process is removed the ligamentum flavum and hypertrophic buildup most commonly associated with degenerative stenosis and instability can generally be removed exposing the lateral dural sac as necessary. Most central disc protrusions have been successfully removed as well as superior or inferior fragments.

Preferably, and as one of skill in the art will appreciate, an intermuscular plane of exposure provides easy access to the spine, minimizes disruption to the erector spinae and multifidus and avoids damage to the neurovascular supply of posterior musculature. The present invention is particularly useful in performing an instrumented transforaminal interbody and facet fusion performed while detaching only the insertion of the multifidus to the mamillary process at the level of fusion. In a preferred embodiment, the retractor 10 of the present invention hooks on the lateral facet cephalade to the transverse process, retracting the longissimus laterally. In such a manner, the superomedial transverse process and lateral facet is free of muscular attachment allowing palpation of the local anatomy for pedicle screw placement. Preferably, the screw is placed just cephalade to the assessory process avoiding any muscle detachment being required. At the caudal vertebrae, the retractor may be hooked against the multifidus below the transverse process allowing visualization of the extent of fixation desired. Using the present invention, it is possible to perform an instrumented lumbar fusion comparable to that accomplished with a mid-line approach, but with much less invasive paramedian approach, requiring decreased neurovascular and muscle dissection and sparing adjacent segments.

To provide further written description and enablement support for the present invention, the following U.S. patents are incorporated in their entireties by this reference: U.S. Pat. Nos. 5,891,147; 6,270,498; 6,080,155; 6,245,072; 5,895,352 and 6,206,826.

The present method and device is useful in intermuscular foraminal facet retraction. In such embodiment, the retractor 10 is configured to have a depth ranging from between about 2 to about 10 cm and the retractor 10 has a hook or prominence 16 associated therewith so as to engage a lateral facet or muscle so as to maintain the retractor position. The retractor blade 14 is angled and has a sufficient depth to provide adequate retraction for screw placement. The engagement of the facet or deep muscle provides a mechanical advantage such that the retraction operation is made easier and the retractor 10 can be maintained in a desired position. The present invention also finds application in a transforaminal retraction where a lateral retractor engages a rod to maintain a desired position or instrumentation. Alternatively, a medial retraction is accomplished using a medial retractor that engages a rod laterally or that engages the instrumentation. The medial retractor retracts muscle medially and provides a working area medial to the rod in the range of 10 to 20 mm. The medial lateral portion engages the rod, providing mechanical advantage in pulling muscle medially and to maintain the desired position of the retractor 20. In alternative embodiments, instrumentation may be engaged, such as a screw or projection from a screw, to provide similar muscle retraction.

While various embodiments of the present invention have been described in detail, it will be apparent that further modifications and adaptations of the invention will occur to those skilled in the art. It is to be expressly understood that such modifications and adaptations are within the spirit and scope of the present invention.

What is claimed is:

1. A surgical retractor device, comprising:
a handle and a blade, said blade angled with respect to said handle and having first and second faces, said second face having at least two toothed structures oriented co-planar with said second face, said at least two toothed structures situated proximate to at least one indentation, said at least two toothed structures and said at least one indentation located along a lateral edge of said second face.

2. The device as claimed in claim 1, wherein said first face is substantially perpendicular to said second face.

3. The device as claimed in claim 1, wherein said at least two toothed structures and said at least one indentation are located along a lower portion of said lateral edge.

4. The device as claimed in claim 1, wherein said at least two toothed structures and said at least one indentation are located along a forward projecting position of said lateral edge of said second face.

5. The device as claimed in claim 1, wherein said at least one indentation is substantially semi-circular in shape.

6. A surgical retractor device for use with a rod implant, comprising:
a handle and a blade, said blade angled with respect to said handle and having first and second faces, said first face being substantially perpendicular to said second face, said second face having at least two toothed structures oriented co-planar with said second face, said at least two toothed structures situated adjacent to at least one indentation, said at least one indentation sized for stabilizing the retractor against the rod implant, said at least two toothed structures and said at least one indentation located along a lateral edge of said second face.

7. The device as claimed in claim 6, wherein said at least two toothed structures and said at least one indentation are located along a lower portion of said lateral edge.

8. The device as claimed in claim 6, wherein said at least two toothed structures and said at least one indentation are located along a forward projecting position of said lateral edge of said second face.

9. The device as claimed in claim 6, wherein said at least one indentation is substantially semi-circular in shape.

* * * * *